United States Patent [19]

Beck

[11] Patent Number: 5,073,366
[45] Date of Patent: Dec. 17, 1991

[54] ANALGESIC COMPOSITION USEFUL IN PROVIDING A TEMPORARY RELIEF FROM SYMPTOMS OF ARTHRITIS

[76] Inventor: Fred Beck, P.O. Box 693, 999 Old Town Rd., Coram, N.Y. 11727

[21] Appl. No.: 358,856

[22] Filed: May 30, 1989

[51] Int. Cl.$^5$ ............ A61K 31/78; A61K 47/00
[52] U.S. Cl. ............ 424/720; 514/772; 514/783; 514/825; 514/906; 514/729; 514/731; 514/789; 424/195.1
[58] Field of Search ............ 424/81; 514/772, 783, 514/825, 887, 906

[56] References Cited

U.S. PATENT DOCUMENTS

| | | | |
|---|---|---|---|
| 4,307,109 | 12/1981 | Arbir et al. | 514/425 |
| 4,383,986 | 5/1983 | Dubash et al. | 424/443 |
| 4,540,572 | 9/1985 | Seth | 424/81 |
| 4,702,916 | 10/1987 | Geria | 424/400 |
| 4,844,902 | 7/1989 | Grohe | 424/449 |
| 4,847,071 | 7/1989 | Bissett et al. | 424/59 |
| 4,863,725 | 9/1989 | Deckner et al. | 424/81 |

OTHER PUBLICATIONS

Merck Index, 1983, p. 563.

Lublanezki et al., Handbook of Non prescription Drugs, p. 547, 1986.

Primary Examiner—Thurman K. Page
Assistant Examiner—G. S. Kishore
Attorney, Agent, or Firm—Edwin D. Schindler

[57] ABSTRACT

An analgesic composition useful in providing temporary relief from the symptoms of arthritis is disclosedng having the following components in approximately the stated weight-percentages ranges:

| | |
|---|---|
| Water (Deionized) | 86.00–95.35% by weight; |
| Carbopol 934 | 0.5–2.00% by weight; |
| Methylparaben | 0.1–0.40% by weight; |
| Propylparaben | 0.05–0.20% by weight; |
| Hampene 100 | 0.05–0.20% by weight; |
| Aloe Vera Gel | 0.05–2.00% by weight; |
| Benzyl Alcohol | 0.30–1.20% by weight; |
| Camphor (U.S.P.) | 0.50–2.00% by weight; |
| Menthol (U.S.P.) | 1.00–4.00% by weight; |
| 90 by weight; | |
| Eugenol | 0.10–0.60% by weight; |
| Witch Hazel | 0.05–1.50% by weight; |
| Isopropyl Alcohol | 0.05–1.50% by weight; |
| Eucalyptus Oil | 0.50–2.00% by weight; |
| Uyimhighdamine | 0.50–2.00% by 0.10–0.40% |

4 Claims, No Drawings

ANALGESIC COMPOSITION USEFUL IN PROVIDING A TEMPORARY RELIEF FROM SYMPTOMS OF ARTHRITIS

The present invention relates, generally, to an analgesic composition useful in temporarily relieving the effects of arthritis. More particularly, the present invention relates to an analgesic composition, preferably in the form of a gel, which is to be applied externally by a patient to areas of arthritic pain.

It is, therefore, an object of the present invention to provide an analgesic composition useful in providing temporary relief from the symptoms of arthritis that is both safe and effective.

It is a further object of the present invention to provide an analgesic gel preparation, useful in the temporary relief of arthritic pain, which is economical to manufacture and which may be dispensed without a prescription.

The foregoing and related objects are achieved by an analgesic composition comprising the following components:

| Component | Percentage (Preferred) | Percentage (Range) |
| --- | --- | --- |
| Water (Deionized) | 90.69 | 86.00–95.35 |
| Carbopol 934 | 1.00 | 0.5–2.00 |
| Methylparaben | 0.20 | 0.1–0.40 |
| Propylparaben | 0.10 | 0.05–0.20 |
| Hampene 100 | 0.10 | 0.05–0.20 |
| Aloe Vera Gel | 1.00 | 0.50–2.00 |
| Benzyl Alcohol | 0.60 | 0.30–1.20 |
| Camphor (U.S.P.) | 1.00 | 0.50–2.00 |
| Menthol (U.S.P.) | 2.00 | 1.00–4.00 |
| Thymol | 0.20 | 0.10–0.60 |
| Eugenol | 0.30 | 0.10–0.60 |
| Witch Hazel | 0.50 | 0.05–1.50 |
| Isopropyl Alcohol | 0.10 | 0.05–1.50 |
| Eucalyptus | 1.00 | 0.50–2.00 |
| Triethanolamine | 1.00 | 0.50–2.00 |
| Quaternium-15 | 0.20 | 0.10–0.40 |

In a preferred embodiment of the invention, the composition may further include a color dye, e.g., a sufficient quality of FD & C Red #40, for example, about 0.1% of the total composition. The coloring of the inventive composition is, however, optional.

Moreover, it should be recognized that variations beyond the foregoing percentage ranges are, to some extent, possible.

The composition of the present invention is preferred produced by way of the following procedure:

In a stainless steel jacketed kettle, equipped with a lightening mixer and with sweep agitation, the manufacturing process commences with the addition of deionized water. Thereafter, carbopol 934 is slowly added, preferably in a sprinkling mode using the lightnin mixer until the solution, or working batch, is uniform. Using sweep agitation, the batch is heated to approximately 72° C.

Thereafter, methylparaben, propylparaben, Hampene-100 (trademark for tetrasodium ED & A) and aloe vera gel, in conformance with the foregoing percentages, are added to the working batch. The working batch is then cooled to approximately 45° C., at which time benzyl alcohol, camphor, menthol, thymol, eugenol, witch hazel, isoproproyl alcohol and eucalyptus oil are added to the batch in conformance with the foregoing percentages. The working batch is then uniformly mixed.

At this point, as an optional step in the process, coloring may be added to the batch, e.g., a sufficient quality of, for example, FD & C Red #40. The purpose of the coloring is to render the composition of the invention more pleasing, visually, to the user. The use of coloring is not required and, if any coloring is added to the composition of the invention, it should, of course, be inert. The quality of coloring added, if any, should be added to match the color of a known standard for that particular color. It is contemplated that if any coloring is utilized in combination with the present invention, that such coloring component would constitute approximately 0.1% by weight of the total composition.

Finally, following the addition of a coloring component to the working batch, triethanolamine and quaternium-45 are added to the batch, at 45° C., in accordance with the foregoing composition percentages. The batch is then preferably cooled to 30° C., and evaluated, before being allowed to reach room temperature.

While only several embodiments of the present invention have been shown and described, it will be obvious to those of ordinary skill in the art that many modifications may be made to the present invention without departing from the spirit and scope thereof.

What is claimed is:

1. A composition useful in providing temporary relief from symptoms of arthritis, comprising:

| | |
| --- | --- |
| Water (Deionized) | 86.00–95.35% by weight; |
| Carbopol 934 (cross-linked acrylic acid polymer) | 0.5–2.00% by weight; |
| Methylparaben | 0.1–0.40% by weight; |
| Propylparaben | 0.05–0.20% by weight; |
| Hampene 100 (tetrasodium EDTA) | 0.05–0.20% by weight; |
| Aloe Vera Gel | 0.50–2.00% by weight; |
| Benzyl Alcohol | 0.30–1.20% by weight; |
| Camphor (U.S.P.) | 0.50–2.00% by weight; |
| [Methol] Menthol (U.S.P.) | 1.00–4.00% by weight; |
| Thymol | 0.10–0.60% by weight; |
| Eugenol | 0.10–0.60% by weight; |
| Witch Hazel | 0.05–1.50% by weight; |
| Isopropyl Alcohol | 0.05–1.50% by weight; |
| [Euclayptus] Eucalyptus Oil | 0.50–2.00% by weight; |
| Triethanolamine | 0.50–2.00% by weight; and, |
| Quaternium-15 (N-(3-chloroallyl)hexaminium chloride) | 0.10–0.40% by weight. |

2. The composition according to claim 1, wherein

| | |
| --- | --- |
| Water (Deionized) | 90.69% by weight; |
| Carbopol 934 (cross-Linked acrylic acid polymer) | 1.00% by weight; |
| Methylparaben | 0.20% by weight; |
| Propylparaben | 0.10% by weight; |
| Hampene 100 (tetrasodium EDTA) | 0.10% by weight; |
| Aloe Vera Gel | 1.00% by weight; |
| Benzyl Alcohol | 0.60% by weight; |
| Camphor (U.S.P.) | 1.00% by weight; |
| Menthol (U.S.P.) | 2.00% by weight; |
| Thymol | 0.20% by weight |
| Eugenol | 0.30% by weight; |
| Witch Hazel | 0.50% by weight; |
| Isoproyl Alcohol | 0.10% by weight; |
| Eucalyptus | 1.00% by weight; |
| Triethanolamine | 1.00% by weight; and, |
| Quaternium-15 (N-(3-chloroallyl) hexaminium chloride) | 0.20% by weight. |

3. The composition according to claim 1, further comprising a coloring component.

4. The composition according to claim 3, wherein said coloring component is FD & C Red #40.

* * * * *